United States Patent
Gao et al.

(10) Patent No.: US 6,221,985 B1
(45) Date of Patent: Apr. 24, 2001

(54) SOLUTION POLYMERIZATION OF ETHYLENE

(75) Inventors: Xiaoliang Gao; Qinyan Wang; Rupert Edward von Haken Spence; Stephen John Brown; Peter Zoricak, all of Calgary (CA)

(73) Assignee: Nova Chemical (International) S.A (CH)

( * ) Notice: Subject to any disclaimer, the term of this patent is extended or adjusted under 35 U.S.C. 154(b) by 0 days.

(21) Appl. No.: 09/229,861

(22) Filed: Jan. 13, 1999

(30) Foreign Application Priority Data

Feb. 1, 1998 (CA) ................................................ 2228802

(51) Int. Cl.$^7$ ................................. C08F 4/44; C08F 4/58
(52) U.S. Cl. .......................... 526/127; 526/160; 526/943; 526/352; 556/53; 502/152
(58) Field of Search ..................... 526/161, 172, 526/348.6, 352, 126, 127, 160; 556/53; 502/104, 152

(56) References Cited

U.S. PATENT DOCUMENTS

| | | |
|---|---|---|
| 4,404,344 | 9/1983 | Sinn et al. . |
| 5,055,438 | 10/1991 | Canich . |
| 5,198,401 | 3/1993 | Turner et al. . |
| 5,324,800 | 6/1994 | Welborn, Jr. et al. . |
| 5,350,723 | 9/1994 | Neithamer et al. . |
| 5,387,568 | 2/1995 | Ewen et al. . |
| 5,589,555 | 12/1996 | Zboril et al. . |
| 5,625,016 | 4/1997 | Schiffino et al. . |
| 5,631,391 | * 5/1997 | Canich et al. ........................ 526/11 |
| 5,635,573 | * 6/1997 | Harrington et al. .................. 526/170 |

FOREIGN PATENT DOCUMENTS

94/80683  3/1994 (JP) .

OTHER PUBLICATIONS

Edward M. Dexheimer and Leonard Spialter, "Tri–t–butyl-silane: Synthesis, Physical Properties, Derivatives, and Reactivity Towards Ozonolysis, Chlorination, Fluorination and Hydrolysis", Journal of Organometallic Chemistry, 102, 1975, pp. 21–27, Printed in The Netherlands.

John A. Soderquist, Jaime Vaquer, Michael J. Diaz, Anil M. Rane, "Triisopropylsilanol: A New Type of Phase Transfer Catalyst for Dehydrohalogenation," Tetrahedron Letters, vol. 37, No. 11, pp. 2561–2564, 1996. Printed in Great Britain.

* cited by examiner

*Primary Examiner*—Donald R. Wilson
*Assistant Examiner*—R. Harlan
(74) *Attorney, Agent, or Firm*—Kenneth H. Johnson

(57) ABSTRACT

A medium pressure process for the solution polymerization of ethylene at a temperature of from 80° C. to 250° C. in the presence of a catalyst system comprising (1) a catalyst component which is a group 4 metal complex having a delocalized, cyclic, pi-bonded ligand, a (defined, specific) heteroligand and one or two activatable ligands; and (2) an ionic activator which does not contain an active proton. The catalyst component is unbridged and easily synthesized. It is highly active in solution polymerization when properly activated (but is not active when used in combination with an alumoxane). Preferred catalyst systems contain an unbridged monocyclopentadienyl titanium (IV) complex and triphenylcarbenium tetrakis (pentafluorophenyl) borate.

12 Claims, No Drawings

SOLUTION POLYMERIZATION OF ETHYLENE

FIELD OF THE INVENTION

This invention relates to a high temperature process for the solution polymerization of ethylene using (1) a catalyst which is a group 4 metal complex having a delocalized, cyclic pi-bonded ligand (such as a cyclopentadienyl ligand), a heteroatom-containing ligand; and (2) an ionic activator which does not contain an active proton and which does not cause the elimination of the heteroatom-containing ligand.

BACKGROUND OF THE INVENTION

Solution polymerization processes are commercially used to prepare a wide variety of ethylene polymers, ranging from crystalline polyethylene plastics to amorphous ethylene-propylene elastomers. It is desirable to operate these processes at high temperatures because increasing the polymerization temperature can (a) improve the rate of polymerization; (b) facilitate the removal of the enthalpy of polymerization (i.e. reactor cooling systems generally become more thermodynamically efficient as the temperature gradient between the reactor and the cooling system is increased); (c) lower the viscosity of the polymer solution; and (d) reduce the amount of energy required to recover the polymer from the solvent. Such solution polymerization reactions often employ a catalyst system which contains a group 4 or group 5 metal, especially titanium and/or vanadium. The catalysts may be comparatively simple transition metal molecules (especially transition metal halides or alkoxides which are used in the so-called Ziegler-Natta catalyst systems) or comparatively more complex mono or bis cyclopentadienyl organometallic molecules which are generally referred to as "metallocenes".

Metallocenes are the catalysts of choice when it is desired to produce ethylene copolymers having uniform comonomer incorporation and a narrow molecular weight distribution. However, most metallocene catalysts are quite temperature sensitive (i.e. the molecular weight of the polymers produced with metallocene catalysts tends to drop to undesirable low values as the temperature is increased under solution polymerization conditions). It is generally theorized that this temperature dependency is a function of a temperature-sensitive beta hydride elimination reaction (and evidence of this is found in the observation that many metallocene catalysts function very well at high temperatures if high ethylene pressures are also used—as in a high pressure or bulk polymerization). However, the maximum ethylene concentration available to the catalyst in a solution polymerization is limited by the solubility of ethylene in the solvent—with the result that many metallocene catalysts are not suitable for use in a solution process. Simply put, many metallocene catalysts don't do the job at the preferred (high) operating temperatures for a solution process.

This problem can sometimes be mitigated using a metallocene catalyst having a bridged ligand—especially those catalysts which incorporate the so-called Bercaw ligand (also known as "constrained geometry" catalysts—see U.S. Pat. No. ("USP") 5,055,438 to Canich and U.S. Pat. No. 5,350,723 to Neithamer et al. However, bridged ligands are difficult and expensive to synthesize. Accordingly, there is a need for comparatively simple unbridged metallocene catalysts for solution polymerizations.

Unbridged catalysts having one cyclopentadienyl ligand and one nitrogen-containing ligand have been disclosed in the art. For example, U.S. Pat. No. 5,625,016 (Schiffino et al) addresses this need and teaches a high temperature solution polymerization process which employs a catalyst that is an unbridged group 4 metal complex having a bulky cyclopentadienyl ligand and a bulky group 15 heteroatom ligand. The use of the bulky cyclopentadienyl ligand is essential to the Schiffino et al catalyst. [Schiffino et al note that Japanese Kokai 94/80683 ("JP '683") discloses a propylene polymerization catalyst having a non-bulky cyclopentadienyl ligand and a bulky group 15 heteroatom ligand. Schiffino et al provide experimental data which clearly illustrate that a catalyst of the JP '683 reference is not a suitable catalyst for the high temperature solution copolymerization of ethylene. However, Schiffino et al provide inventive data which illustrates that the use of a bulky cyclopentadienyl ligand does produce a useful catalyst.]

The group 15 heteroatom ligand initially disclosed in the JP '683 reference (and subsequently employed by Schiffino et al) is characterized by having a nitrogen atom which is bonded to the transition metal and substituted with two bulky substituents (in particular, two bulky trimethyl silyl groups).

In a copending and commonly assigned application (Stephan et al) there is disclosed a solution polymerization catalyst having a cyclopentadienyl ligand and a phosphinimine ligand. The phosphinimine ligand has a nitrogen atom which is bonded to the transition metal and doubly bonded to a phosphorous (v) atom. Thus, there is only one substituent on the nitrogen atom of the phosphinimine ligands disclosed by Stephan et al (namely the phosphorous (v) atom) whereas the heteroatom ligands taught by Schiffino et al and JP '683 have two substituents on the nitrogen ligand.

Schiffino et al and Stephan et al both disclose the use of two alternative activators, namely (1) alumoxanes; and (2) "ionic activators". Alumoxanes were discovered to be excellent activators for metallocenes by Kaminsky and Sinn, as claimed in U.S. Pat. No. 4,404,344. Hlatky and Turner subsequently discovered that ionic activators function well with bis(cyclopentadienyl) metallocene complexes (see for example, U.S. Pat. No. 5,198,401).

Although the Schiffino et al and Stephan et al references described above do disclose catalysts having utility in solution polymerizations, there is still a need for other simple, robust catalysts which function well in solution polymerizations.

SUMMARY OF THE INVENTION

The present invention provides a medium pressure process for the solution polymerization of ethylene at a temperature of from 80° C. to 250° C. in the presence of a catalyst system comprising:

(1) an unbridged catalyst compound defined by the formula:

wherein:
"$Cp$" is a cyclic ligand which forms a delocalized pi-bond with M;
M is a metal selected from Ti, Hf and Zr;
X is an activatable ligand;
n is 2 when M is Hf and n is 1 or 2 when M is Ti or Zr;
L is a heteroligand defined by the formula:

wherein:
    µ is a heteroatom selected from O and S and wherein said heteroatom is bonded to M;
    $R_1$, $R_2$ and $R_3$ are substituents on said Si atom; and
(2) an ionic activator which does not contain an active proton.

The catalyst component of this invention is unbridged and very easy to synthesize. However, the catalyst is not active in the presence of a conventional alumoxane activator. While not wishing to be bound by any particular theory, it is believed that alumoxanes (which have Lewis acid character) interact or react with the basic heteroatom-ligand, and that this acid-base reaction (or interaction) produces an inactive species. Thus, the present invention excludes the use of alumoxanes but requires a so-called "ionic activator".

DETAILED DESCRIPTION OF THE PREFERRED EMBODIMENT

Detailed description s of (1) Process Conditions; (2) the Catalyst Component; and (3) the Ionic Activator for the Catalyst Component, are provided below.

1. Process Conditions

The polymerization process according to this invention can be described as a medium pressure solution polymerization process. The process uses ethylene and may further include other monomers which are copolymerizable therewith (especially other alpha olefins such as propylene, butene, hexene or octene). It is highly preferred that the process be used to prepare linear low density polyethylene ("LLDPE") plastic or plastomers (i.e. copolymers having a density of less than 0.935 g/cc) via the copolymerization of a major portion of ethylene with a minor portion of butene or octene.

In a medium pressure solution polymerization, the monomers may be dissolved in the solvent prior to being fed to the reactor and/or the monomers may (also) be directly fed to the reactor. Exemplary (i.e. illustrative but non-limiting) solvents include $C_6$ to $C_{10}$ hydrocarbyls such as methyl pentanes, hexanes, cyclohexane, naphtha, gasolines and commercially available solvents such as those sold under the trademark ISOPAR by Exxon. The solvent and monomers are generally purified to remove poisons (such as water, carbon monoxide, acetylene, oxygen) prior to being introduced into the reactor. The purification procedures are well known to those skilled in the art and may use such standard practices as the use of molecular sieves and/or alumina beds. In some instances an organometallic scavenger agent (such as a minor amount of a transition metal alkyl; an alkyl aluminum or an alumoxane) may be directly added to the reactor for additional in-situ purification. However, a great deal of care must be taken when using organometallic scavengers as they may react with (and deactivate) the catalyst system (in particular, the alumoxanes appear to deactivate the catalyst component, as will be described in the examples).

The reactor feeds (solvent and monomers) may be heated prior to addition to the reactor. However, in many instances it is desired to remove the heat generated by the polymerization reaction from the system (in which case the reactor feeds may be added at near ambient conditions as a source of reactor cooling).

In general, the catalyst and activator are mixed with solvent prior to addition to the reactor. In some cases it may be desirable to allow the catalyst and activator to react with each other prior to addition to the reactor. If desired, this may be accomplished by the "in-line" mixing technique described in U.S. Pat. No. 5,589,555 (issued to DuPont Canada).

The reactor system may include one or more autoclaves (also known as constantly stirred tank reactors ("CSTRs")) and/or a tubular reactor. The use of two or more reactors may be employed to produce polymers having varying molecular weight distribution.

As used herein, the term "medium pressure solution process" refers to a polymerization carried out in a solvent for the polymer at an operating temperature of from 100 to 320° C. (especially from 120 to 220° C.) and a total pressure of from 4 to 25 mega Pascals. Additional details concerning the medium pressure solution polymerization process are well known to those skilled in the art and are widely described in the literature.

2. Catalyst System: Catalyst Component+Activator

The catalyst system must contain a catalyst component and an ionic activator, as defined below.

2.1 Catalyst Component

As previously noted, the catalyst component is defined by the formula:

$$^I\!CpMLX_n$$

wherein:
    "$^I\!Cp$" is a cyclic ligand which forms a delocalized pi-bond with M;
    M is a metal selected from Ti, Hf and Zr;
    X is an activatable ligand;
    n is 2 when M is Hf and n is 1 or 2 when M is Ti or Zr;
    L is a heteroligand defined by the formula:

$$—(\mu)SiR_1R_2R_3$$

wherein:
        µ is a heteroatom selected from O and S and wherein said heteroatom is bonded to M;
        $R_1$, $R_2$ and $R_3$ are substituents on said Si atom.

The "$^I\!Cp$ ligand" is cyclic and forms a delocalized pi-bond with the group 4 transition metal M. An exemplary (i.e. illustrative but non-limiting) list of "$^I\!Cp$ ligands" includes substituted (or unsubstituted) cyclopentadienyl ligands, substituted (or unsubstituted) indenyl ligands and cyclic hetero ligands in which one or more of the carbon atoms in the cycle is replaced with a heteroatom such as boron, nitrogen or phosphorus (for example, a so-called "phosphole" ligand which contains four carbon atoms and one phosphorus atom in the ring).

The use of "substituents" on such cyclic ligands is well known and is described, for example, in U.S. Pat. No. 5,324,800 (Welborn). An exemplary list of substituents for such $^I\!Cp$ ligands includes $C_{1-20}$ hydrocarbyl groups; substituted $C_{1-20}$ hydrocarbyl groups wherein one or more hydrogen atoms is replaced by a halogen; an amido group, a phosphido group, or an alkoxy group.

For reasons of cost and simplicity, it is especially preferred that the $^I\!Cp$ ligand is a cyclopentadienyl or indenyl ligand.

The heteroligand L is defined by the formula:

$$—(\mu)SiR_1R_2R_3$$

where the — denotes a bond to the transition metal and µ is sulfur or oxygen.

It is particularly preferred that µ is oxygen (because the resulting family of catalyst components has been discovered to be exceptionally active when used at very low concentrations in continuous flow solution polymerizations, as illustrated in the Examples).

The substituents on the Si atom, namely $R_1$, $R_2$ and $R_3$ are required in order to satisfy the bonding orbital of the Si atom. The use of any particular substituent $R_1$, $R_2$ or $R_3$ is not especially important to the success of this invention. It is preferred that each of $R_1$, $R_2$ and $R_3$ is a $C_{1-4}$ hydrocarbyl group such as methyl, ethyl, isopropyl or tertiary butyl (simply because silanes having such hydrocarbyl groups are readily available items of commerce).

The catalyst component also contains at least one "activatable" ligand. The term activatable ligand refers to a ligand which can be abstracted by the ionic activator to a catalytically active state. Exemplary activatable ligands include saturated alkyls (especially those having from 1 to 4 carbon atoms, preferably methyl); hydrogen; cycloalkyls/aryls (such as benzyl), alkyls, and butadiene.

It will be appreciated by those skilled in the art that the number of activatable ligands will directly depend upon whether the activatable ligand is mono or di valent and the oxidation state of the metal. For example, a Ti(III) (Ti in the $3^+$ oxidation state) would have one monoanionic ligand in addition to the $^iCp$ ligand and the heteroligand (for example, one methyl group) and Ti(IV) would have two activatable ligands. It is preferred that the group 4 metal be in the $4^+$ oxidation state and have two monoanionic activatable ligands.

2.2 Ionic Activator

As previously noted the catalyst systems of this invention must contain an ionic activator. The term "ionic activator" refers to a complex which reacts with the catalyst component to form an active catalyst system which is schematically illustrated by the following formula:

[Cat$^+$][An$^-$]

where:

Cat$^+$ is a cationic species derived by abstracting an activatable ligand from the catalyst component; and An$^-$ is a non-coordinating, compatible anion which charge stabilizes the cationic species (i.e. the anion does not coordinate so strongly as to prevent the monomer insertion reaction which is required for polymerization).

Alumoxanes are not suitable as activators for the catalyst components of this invention. Whilst not wishing to be bound by any particular theory, it is believed that alumoxanes (which are acidic in the sense of being Lewis acids) cause decomposition of the catalyst component via attack at the basic bond between the metal and the oxygen (or sulfur) atom of the heteroligand.

The ionic activators used in this invention don't contain an active proton but contain a carbonium, oxonium or sulfonium cation (as described in U.S. Pat. No. 5,387,568 to Ewen). Preferred ionic activators produce a bulky anion ("An$^-$") which is a perfluorinated phenyl borate (borates are also referred to in the literature as "boronates" or simply by the suffix "boron"). An exemplary list includes: tri(methylphenyl)phosphonium tetrakispentafluorophenylborate, tri(dimethylphenyl)phosphonium tetraphenylborate, triphenylcarbenium tetrakis(pentafluorophenyl)borate, triphenylcarbenium tris(pentafluorophenyl)phenyl borate and triphenylcarbeniumtris(pentafluorophenyl)4-trimethylsilyl-2,3,5,6-tetrafluorophenylborate.

EXAMPLES

Further details are provided by the following non-limiting examples. Part A describes catalyst component synthesis and Part B illustrates polymerization.

The following abbreviations are used in the examples: $^tBu$ for tertiary-butyl; Me for methyl; Cp for unsubstituted cyclopentadienyl; EtOH for ethanol; (aq) for aqueous; $^iPr$ for isopropyl; MAO for methylalumoxane; Ph for phenyl; and *Cp for pentamethyl cyclopentadienyl.

PART A

Catalyst Component Synthesis

Tri-tert-butylsilane was synthesized according to literature preparation (*J. Organometallic Chem.*, 102, 21–27, 1975).

Synthesis of Tri-tert-butylsilanol

Into a $CH_2Cl_2$ solution (100 milliliters (mL)) of $^tBuSiH$ (4.11 grams (g), 20.5 millimoles (mmol)) was slowly added (via syringe) $Br_2$ (1.06 mL, 20.5 mmol). The yellow solution was then stirred for 1 hour with periodic venting of HBr. Methylene chloride was removed under reduced pressure leaving a pale yellow sticky solid which was used without further purification.

To the sticky solid was added a KOH (4.6 g, 82 mmol) solution (30 mL EtOH/10 mL $H_2O$) and then the solution was refluxed for 36 hours under argon pressure at 130° C. The solution is then cooled and 30 mL of solvent is distilled off at ambient pressure. The remaining solution was diluted with 200 mL of $H_2O$ and acidified with $HCl_{(aq)}$ to a pH of ~2. The product is then extracted into diethyl ether (4×125 mL) and dried over $Na_2SO_4$. All solvent was then removed under reduced pressure leaving a pale yellow oil as the final product which was further purified by a vacuum transfer to another flask. Yield 3.86 g. Proton nuclear magnetic resonance spectrum ($^1H$-NMR) in deuterated toluene ($C_7D_8$, δ): 1.16 (s, peak area=27 protons (27H).

Synthesis of Cyclopentadienyl(tri-t-butylsi loxy)Titani um Dichloride (or "CpTiOSi$^tBu_3Cl_2$")

NaOSi$^tBu_3$ (0.502 g, 2.106 mmol, prepared by reacting Na and $^tBu_3SiOH$ in refluxing hexane) in toluene (20 mL) was added to a toluene solution (20 mL) of $CpTiCl_3$ (0.462 g, 2.106 mmol) at −78° C. The solution was warmed to 23° C. and stirred for about 5 hours. The solution was pumped to dryness and the residue was extracted with hexane. The hexane solution was concentrated to ~2 mL and the product crystallized as yellow-orange crystals at −70° C. Yield was 0.79g, 94%. $^1H$ NMR ($C_7D_8$, δ): 6.22 (s, 5H), 1.17 (s, 27H).

Synthesis of Cyclopentadienyl(tri-tert-butylsiloxy) Titanium Dimethyl (or "CpTiOSi$^tBu_3Me_2$")

A solution of MeMgBr (3M, 0.9 mL, 2.7 mmol) in ether was added to a solution of Cp($^tBu_3SiO$)TiCl$_2$ (0.392 g, 0.98 mmol) in toluene (30 mL) at −78° C. The solution was warmed to 23° C., stirred for 1 hour and pumped to dryness. The residue was extracted with hexane (3×30 mL) and the hexane filtrate was pumped to dryness to give an orange oil (352 mg, 100% yield). $^1H$ NMR ($C_7D_8$, δ): 6.00 (s, 5H), 1.21 (s, 27H), 0.74(s, 6H).

Synthesis Pentamethylcyclopentadienyl(tri-tert-butylsiloxy) Titanium Dimethyl (or "*CpTiOSi$^tBU_3Me_2$")

To a solution of *CpTiMe$_3$ (0.456 g, 2.00 mmol) in 50 mL of hexanes at −78° C. was added dropwise $^tBu_3SiOH$ (0.433 g, 2 mmol) in 40 mL of hexanes. The solution was then allowed to reach room temperature over 30 minutes and was then heated to 50° C. at which point $CH_4$ liberation was observed. The solution was then stirred at 50°C. for an additional 30 minutes and then all hexanes were removed under reduced pressure to give Me$_5$Cp($^tBu_3SiO$)TiMe$_2$ as a bright yellow solid. Yield was quantitative. $^1H$ NMR ($C_7D_8$, δ): 1.81 (s, 15H), 1.31 (s, 27H), 0.54 (s, 6H).

Synthesis of Pentamethylcyclopentadienyl(tri-isopropylsiloxy) Titanium Dimethyl (or "*CpTiOSi($^iPr$)$_3Me_2$")

Tri-iso-propylsilanol was synthesized according to literature preparation (*Tetrahedron Letters*, Vol. 37, No 15,2561–2564, 1996).

To a solution of Me$_5$CpTiMe$_3$ (0.541 g, 2.37 mmol) in 50 mL of hexanes at –78° C. was added dropwise $^i$Pr$_3$SiOH (0.413 g, 2.37 mmol) in 40 mL of hexanes. The solution was then allowed to reach room temperature over 30 minutes and was then heated to 50° C. The solution was then stirred at 50° C. for an additional 16 hours and then all hexanes were removed under reduced pressure to give Me$_5$Cp($^i$Pr$_3$SiO)TiMe$_2$ as a dark yellow oil which crystallizes at –30° C. Yield was quantitative. $^1$H NMR (C$_7$D$_8$, δ): 1.82 (s, 15H), 1.23 (d, 21 H), 0.51 (s, 6H).

Synthesis of Cyclopentadienyl(tri-iso-propylsiloxy) Titanium Dichloride (or "CpTiOSi($^i$Pr)$_3$Cl$_2$")

To a solution of CpTiCl$_3$ (0.772 g, 3.52 mmol) in 40 mL of toluene was added dropwise a solution of $^i$Pr3SiOH (0.49 mL, 3.52 mmol) and Et$_3$N (0.49 mL, 3.52 mmol) in 25 mL of toluene at room temperature. The turbid yellow solution was then stirred for 3 days and then all toluene was removed under reduced pressure. The yellow solid was slurried in 40 mL of hexane and filtered to give a clear yellow solution. All hexane was removed under reduced pressure to give a dark yellow oil which crystallized at –30° C. Yield was quantitative. $^1$H NMR (C$_7$D$_8$, δ): 6.19 (s, 5H), 1.06 (m, 21H).

Synthesis of Cyclopentadienyl(tri-iso-propylsiloxy) Titanium Dimethyl (or "CpTIOSi($^i$Pr)$_3$Me$_2$")

To a solution of Cp($^i$Pr$_3$SiO)TiCl$_2$ (1.26 g, 3.52 mmol) in 40 mL of toluene at –78° C. was added using a syringe MeMgBr (3.05 mL, 9.16 mmol). The solution was then allowed to reach room temperature during which time observed color changes were from yellow to yellowish green. The toluene was then filtered to give a clear yellow solution. All solvent was removed under reduced pressure leaving a dark yellow oily product. $^1$H NMR (C$_7$D$_8$, δ): 5.98 (s, 5H), 1.13 (m, 21H), 0.71 (s, 6H).

Synthesis Pentamethylcyclopentadienyl(tri-ethylsiloxy) Titanium Dimethyl (or "*CpTiOSi(Et)$_3$Me$_2$")

To a solution of *CpTiMe$_3$ (0.606 g, 2.65 mmol) in 50 mL of hexanes at –78° C. was added dropwise Et$_3$SiOH (0.351 g, 2.65 mmol) in 40 mL of hexanes. The solution was then allowed to reach room temperature over 30 minutes and was then heated to 50° C. The solution was then stirred at 50° C. for an additional 16 hours and then all hexanes were removed under reduced pressure to give Me$_5$Cp(Et$_3$SiO)TiMe$_2$ as a yellow oil. Yield was quantitative. $^1$H NMR (C$_7$D$_8$, δ): 1.81 (s, 15H), 1.14–1.10 (tq, 9H), 0.84–0.72 (qq, 6H), 0.48 (s, 6H).

Synthesis of i-Pr$_3$SiLi

Tri-isopropylsilylthiol, dried over molecular sieves for 4 hours, was distilled under a high static vacuum (10$^{-3}$ torr). The pure thiol was reacted with equal molar amount of n-BuLi in hexane at –70° C., followed by stirring while warming to room temperature. Removal of hexane under vacuum gave the resulting lithium salt in quantitative yield.

Synthesis of Pentamethylcyclopentadienyl(tri isopropylsilyithiolate) Titanium Dichioride (or "*CpTiSSi($^i$Pr)$_3$Cl$_2$")

A toluene slurry of i-Pr3SiSLi (1.71 g, 8.72 mmol) was added to a toluene solution of *CpTiCl$_3$ (2.52 g, 8.72 mmol) at –70° C. with stirring, and subsequently the mixture was allowed to reach room temperature. The solution was pumped to dryness and the solid was extracted with hexane. Crystallization from hexane yielded the dichloride as orange crystals. $^1$H NMR (δ, C$_7$D$_8$): 1.218 (d , 18H), 1.630 (spt, 3H), 2.048 (s, 15H).

Synthesis of Pentamethylcyclopentadienyl(tri isopropylsilylthiolate) Titanium Dimethyl (or "*CpTiSSi($^i$Pr)$_3$Me$_2$")

*CpTiCl$_2$(i-Pr$_3$SiS) (720 g, 1.62 mmol) was dissolved in toluene and MeMgBr (3.32 mmol) was added via an air tight syringe at –70° C. The mixture was allowed to reach room temperature. Toluene was removed and the residue was extracted with hexane. The hexane extract was filtered and dried in vacuo (10$^{-3}$ torr) to give the product as a brown solid. Yield was quantitative. $^1$H NMR (δ, C$_7$D8): 1.094 (s, 6H), 1.270 (d, 18H), 1.450 (spt, 3H), 1.884(s, 15H).

Synthesis of Cyclopentadienyl (tri isopropylsilylthiolate) Titanium Dichloride (or "*CpTiSi($^i$Pr)$_3$Cl$_2$")

A toluene slurry of i-Pr3SiSLi (1.19 g, 6.04 mmol) was added to a toluene solution of TiCl$_3$(η$_5$-C$_5$H$_5$) (1.325g, 6.05 mmol) at –70° C. After the reaction was allowed to reach room temperature and was stirred for 1 more hour, toluene was removed under vacuum. The solid was extracted with hexane and the hexane extract was filtered and dried in vacuo (10$^{-3}$ torr) to give the product as a red crystalline solid. Yield: 2.17 g, 96%. $^1$H NMR (δ, C$_7$D$_8$): 1.223 (d, 18H), 1.708 (spt, 3H), 6.195 (s, 15H).

The dimethyl derivative of this compound was attempted by methylating the dichloride with MeMgBr. Some decomposition was observed and therefore the product was probably not completely pure.

Solution Batch Reactor (SBR) Results

All the compound s were considered to be extremely oxygen and moisture sensitive. Manipulations were therefore carried out under nitrogen using a glovebox or under argon using Schenk-line techniques. An hydrous toluene was purchased from Aldrich and purified over conventional mole sieves.

The catalysts CpTiOSi$^t$Bu$_3$Cl$_2$ (1) and CpTiOSi$^t$Bu$_3$Me$_2$ (2) used in this study were synthesized as described in Part A and CpTiCl$_3$ was purchased from Aldrich. The catalysts were dissolved in toluene and the catalyst concentrations were between 0.7–5 mg/mL.

Ethylene (99.5%, polymer grade, Praxair) was purified by passage through the mole sieves and alumina. Bulk cyclohexane was purchased and was further purified by passage through the mole sieves and alumina prior to use. Methyl alumoxane ("PMAO-IP") was purchased from Akzo-Nobel and contained 12.9 wt. % of Al.

The SBR was used in the polymerization experiments. The SBR uses a programmable logical control (PLC) system with Wonderware 5.1 software for process control. Ethylene polymerizations were performed in a 500 mL Autoclave Engineers Zipperclave reactor equipped with an air driven stirrer and an automatic temperature control system. All the chemicals were fed into the reactor batchwise in amounts shown in the table below except ethylene which was fed on demand. 79

Example 1

The experiments for CpTiOSi$^t$BU$_3$Cl$_2$ (1) were carried out as follows:

| | |
|---|---|
| Cyclohexane | 216 mL |
| Catalyst concentration | 200 μmol/L |
| Cocatalyst | PMAO-IP; Al/Ti = 300 mol/mol |
| Reaction temperature | 160° C. |
| Reactor pressure | 140 psig total |
| Stirring speed | 2000 rpm |

The catalyst showed no detectable activity at the above conditions. Thus, the experiments were continued by addition of a second loading of catalyst without the second loading of the cocatalyst. The polymerization time was 10 minutes in each experiment. The reactions were terminated by adding 5 mL of methanol to the reactor and trace amounts of polymer were recovered by evaporation of the cyclohexane.

Example 2

The experiment for $CpTiOSi^tBu_3Me_2$ (2) was carried out as follows:

| | |
|---|---|
| Cyclohexane | 216 mL |
| Catalyst concentration | 200 µmol/L |
| Cocatalyst | $[CPh_3][B(C_6F_5)_4]$ ("trityl borate"); 210 µmol/L |
| Scavenger | PMAO-IP 1 mmol/L dissolved in 250 mL of cyclohexane as the scavenger, the solution was stirred for 10 minutes at room temperature, then withdrawn with a canula before the reaction solvent was loaded in |
| Reaction temperature | 160° C. |
| Reactor pressure | 140 psig total |
| Stirring speed | 2000 rpm |

Polymer molecular weights and molecular weight distributions were measured by GPC (Waters 150-C) at 140° C. in 1,2,4-trichlorobenzene calibrated using polyethylene standards.

TABLE 1

Polymerization Activity

| Example | Catalyst | Polymerization activity g PE/mMolcat*hr[1] |
|---|---|---|
| 1 | $CpTiOSi^tBu_3Cl_2$ | trace |
| 2 | $CpTiOSi^tBu_3Me_2$ | 388.62 |
| 3 | $CpTiCl_3$ | 54.22 |

[1]The calculation of polymerization activity is based on the ethylene uptake.

TABLE 2

Polymer Properties

| Example | Catalyst | Mw(*10$^{-3}$) | Mw/Mn |
|---|---|---|---|
| 1 | $CpTiOSi^tBu_3Cl_2$ | — | — |
| 2 | $CpTiOSi^tBu_3Me_2$ | 57.1 | 5.34 |
| 3 | $CpTiCl_3$ | 147.1 | 15.09 |

Polmerization activity of the catalysts $CpTiOSi^tBU_3Cl_2$ and $CpTiOSi^tBu_3Me_2$ is very sensitive to MAO. The catalyst $CpTiOSi^tBu_3Me_2$ (2), when activated with trityl borate (with an extremely low level of alumoxane present as a scavenger) showed a very high initial polymerization rate but quick deactivation. This suggests the possibility of a bimolecular deactivation mechanism which may be mitigated through the use of dilute catalyst concentrations in a continuous flow polymerization (as illustrated in the next section).

PART B

The Continuous Solution Polymerization

All the polymerization experiments described below were conducted on a continuous solution polymerization reactor. The process is continuous in all feed streams (solvent, monomers and catalyst) and in the removal of product. All feed streams were purified prior to the reactor by contact withous absorption media to remove catalyst killing impurities such as water, oxygen and polar materials as is known to those skilled in the art. All components were stored and manipulated under an atmosphere of purified nitrogen.

All the examples below were conducted in a reactor of 71.5 cc internal volume. In each experiment the volumetric feed to the reactor was kept constant and as a consequence so was the reactor residence time.

The catalyst solutions were pumped to the reactor independently and there was no pre-contact between the activator and the catalyst. Because of the low solubility of the catalysts, activators and MAO in cyclohexane, solutions were prepared in purified xylene. The catalyst was activated in-situ (in the polymerization reactor) at the reaction temperature in the presence of the monomers. The polymerizations were carried out in cyclohexane at a pressure of 1500 psi. Ethylene was supplied to the reactor by a calibrated thermal mass flow meter and was dissolved in the reaction solvent prior to the polymerization reactor. If comonomer (for example 1-octene) was used it was also premixed with the ethylene before entering the polymerization reactor. Under these conditions the ethylene conversion is a dependent variable controlled by the catalyst concentration, reaction temperature and catalyst activity etc.

The internal reactor temperature is monitored by a thermocouple in the polymerization medium and can be controlled at the required set point to +/−0.5° C. Downstream of the reactor the pressure was reduced from the reaction pressure (1500 psi) to atmospheric. The solid polymer was then recovered as a slurry in the condensed solvent and was dried by evaporation before analysis.

The ethylene conversion was determined by a dedicated on-line gas chromatograph by reference to propane which was used as an internal standard. The average polymerization rate constant was calculated based on the reactor hold-up time, the catalyst concentration in the reactor and the ethylene conversion and is expressed in l/(mmol*min).

Average polymerization rate $(kp)=(Q/(100-Q))\times(1/[TM])\times(1/HUT)$ where:

Q is the percent ethylene conversion;

[TM] is the catalyst concentration in the reactor expressed in mM; and

HUT is the reactor hold-up time in minutes.

Polymer Analysis

Melt index (MI) measurements were conducted according to ASTM method D-1238-82.

Polymer densities were measured on pressed plaques (ASTM D-1928-90) with a densitometer.

Example 1 (2-180-4)

*$CpTiOSi(^tBu)_3Me_2$ was added to the reactor at $12.0\times10^{-6}$ mol/l along with $Ph_3C\ B(C_6F_5)_4$ (Asahi Glass) at B/Ti=1.00 (mol/mol). The reaction temperature was 160° C. and 2.1 gram/min. of ethylene was continuously added to the reactor. In addition 3.00 m/min. of 1-octene was also fed to the reactor. An ethylene conversion of 93.4% was observed (see Table 1).

Example 2 (2-180-7)

*$CpTiOSi(^tBu)_3Me_2$ was added to the reactor at $3.7\times10^{-6}$ mol/l along with $Ph_3C\ B(C_6F_5)_4$ (Asahi Glass) at B/Ti=1.00 (mol/mol). The reaction temperature was 160° C. and 2.1 gram/min. of ethylene was continuously added to the reactor. An ethylene conversion of 94.4% was observed (see Table 1).

Example 3 (2-187-4)

*CpTiOSi($^t$Bu)$_3$Me$_2$ was added to the reactor at 37.0×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min. of ethylene was continuously added to the reactor. In addition 3.00 ml/min. of 1-octene was also feed to the reactor. An ethylene conversion of 89.8% was observed (see Table 1).

Example 4 (2-187-5)

*CpTiOSi($^t$Bu)$_3$Me$_2$ was added to the reactor at 22.2×10$^{-6}$ mol/l along with Ph$_3$C B(C$_6$F$_5$)$_4$ (Asahi Glass) at B/Ti=1.00 (mol/mol). The reaction temperature was 1600° C. and 2.1 gram/min. of ethylene was continuously added to the reactor. An ethylene conversion of 88.6% was observed (see Table 1).

Example 5 (2-211-5)

*CpTiOSi($^i$Pr)$_3$Me$_2$ was added to the reactor at 9.3×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min. of ethylene was continuously added to the reactor. An ethylene conversion of 90.3% was observed (see Table 1).

Example 6 (2-211-6)

*CpTiOSi($^i$Pr)$_3$Me$_2$ was added to the reactor at 7.4×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min. of ethylene was continuously added to the reactor. In addition 0.50 ml/min. of 1-octene was also feed to the reactor. An ethylene conversion of 91.7% was observed (see Table 1).

Example 7 (2-211-7)

*CpTiOSi($^i$Pr)$_3$Me$_2$ was added to the reactor at 7.4×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min. of ethylene was continuously added to the reactor. In addition 1.00 ml/min. of 1-octene was also feed to the reactor. An ethylene conversion of 90.5% was observed (see Table 1).

Example 8 (2-211-9)

*CpTiOSi($^i$Pr)$_3$Me$_2$ was added to the reactor at 10.2×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min. of ethylene was continuously added to the reactor. In addition 3.00 ml/min. of 1-octene was also feed to the reactor. An ethylene conversion of 89.4% was continuously added to the reactor. An ethylene conversion of 87.3% was observed (see Table 1).

Example 9 (2-216-8)

*CpTiSSi($^i$Pr)$_3$Me$_2$ was added to the reactor at 74.1×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min. of ethylene was continuously added to the reactor. An ethylene conversion of 87.3% was observed (see Table 1).

Example 10 (2-216-9)

*CpTiSSi($^i$Pr)$_3$Me$_2$ was added to the reactor at 83.3×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min. of ethylene was continuously added to the reactor. In addition 2.00 ml/min. of 1-octene was also feed to the reactor. An ethylene conversion of 77.0% was observed (see Table 1).

Example 11 (2-219-2)

*CpTiOSi(Et)$_3$Me$_2$ was added to the reactor at 9.3×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min. of ethylene was continuously added to the reactor. An ethylene conversion of 90.6% was observed (see Table 1).

Example 12 (2-219-7)

*CpTiOSi(Et)$_3$Me$_2$ was added to the reactor at 7.4×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min. of ethylene was continuously added to the reactor. In addition 2.00 ml/min. of 1-octene was also feed to the reactor. An ethylene conversion of 91.6% was observed (see Table 1).

Example 13 (2-219-8)

*CpTiOSi(Et)$_3$Me$_2$ was added to the reactor at 6.5×10$^{-6}$ mol/l along with Ph$_3$C B(C$_6$F$_5$)$_4$ (Asahi Glass) at B/Ti=1.00 (mol/mol). The reaction temperature was 160° C. and 2.1 gram/min. of ethylene was continuously added to the reactor. An ethylene conversion of 89.5% was observed (see Table 1).

Example 14 (2-219-9)

*CpTiOSi(Et)$_3$Me$_2$ was added to the reactor at 9.3×10$^{-6}$ mol/l along with B(C$_6$F$_5$)$_3$ (Boulder Scientific) at B/Ti=2.50 (mol/lmol). The reaction temperature was 160° C. and 2.1 gram/min. of ethylene was continuously added to the reactor. An ethylene conversion of 93.1% was observed (see Table 1).

Comparative Example 15 (1-48-1)

*CpZrCl$_2$ (Strem) was added to the reactor at 37×10$^{-6}$ mol/l along with MMAO-3 (Akzo-Nobel, Al/Ti=400 mol/mol). The reaction temperature was 140° C. and 1.0 gram/min. of ethylene was continuously added to the reactor. An ethylene conversion of 55.5% was observed (see Table 1).

Comparative Example 16 (1-48-2)

*CpZrCl$_2$ (Strem) was added to the reactor at 37×10$^{-6}$ mol/l along with MMAO-3 (Akzo-Nobel, Al/Ti=400 mol/mol). The reaction temperature was 160° C. and 1.0 gram/min. of ethylene was continuously added to the reactor. An ethylene conversion of 35.6% was observed (see Table 1).

Comparative Example 17 (1-48-4)

*CpZrCl$_2$ (Strem) was added to the reactor at 37×10$^{-6}$ mol/l along with MMAO-3 (Akzo-Nobel, Al/Ti=400 mol/mol). The reaction temperature was 160° C. and 2.1 gram/min. of ethylene was continuously added to the reactor. An ethylene conversion of 37.4% was observed (see Table 1).

Comparative Example 18 (1-47-4)

rac-Et(ind)$_2$ZrCl$_2$ (Witco) was added to the reactor at 37×10$^{-6}$ mol/l along with MMAO-3 (Akzo-Nobel, Al/Ti= 400 mol/mol). The reaction temperature was 160° C. and 2.1 gram/min. of ethylene was continuously added to the reactor. An ethylene conversion of 94.6% was observed (see Table 1).

Comparative Example 19 (1-35-6)

rac-Et(ind)$_2$ZrCl$_2$ (Witco) was added to the reactor at 37×10$^{-6}$ mol/l along with MMAO-3 (Akzo-Nobel, Al/Ti= 400 mol/mol). The reaction temperature was 160° C. and 2.1 gram/min. of ethylene and 3.25 ml/min. of 1-octene was continuously added to the reactor. An ethylene conversion of 94.8% was observed (see Table 1).

The data in Table 1 show that the inventive catalysts are extremely active when used at low concentrations in a continuous flow reactor (see especially example 2). The catalysts in which the "heteroligand" is bonded to the metal via oxygen (i.e. examples 1–8 and 11–14) are preferred over the catalysts of examples 9 and 10 because of catalyst activity.

L is a heteroligand defined by the formula:

—($\mu$)SiR$_1$R$_2$R$_3$ wherein:
$\mu$ is a heteroatom selected from O and S and wherein said heteroatom is bonded to M;
R$_1$, R$_2$ and R$_3$ are substituents on said Si atom; and
(2) an ionic activator which does not contain an active proton.

2. The process of claim 1 wherein said $^I$Cp is selected from unsubstituted cyclopentadienyl, substituted cyclopentadienyl, unsubstituted indenyl and substituted indenyl.

3. The process of claim 1 wherein M is titanium.

4. The process of claim 3 wherein said titanium is titanium (IV) and n is 2.

5. The process of claim 1 wherein X is a hydrocarbyl ligand.

6. The process of claim 5 wherein X is methyl.

7. The process of claim 1 wherein said heteroligand is defined by the formula:

—OSiR$_1$R$_2$R$_3$ and each of R$_1$, R$_2$ and R$_3$ is independently selected from the group consisting of ethyl, isopropyl and tertiary-butyl.

TABLE 1

| Example | Total Flow to Reactor (ml/min.) | Catalyst Concentration (mol × 10$^6$) | Ethylene Conversion (%) | Calculated Polymerization Rate (kp) (l/mmol × min.) | Polymer Density (g/cc) | Polymer Melt Index | mn × 10$^{-3}$ | mw × 10$^{-3}$ |
|---|---|---|---|---|---|---|---|---|
| 1 | 27.0 | 12.0 | 93.4 | 442 | 0.873 | 1900 | 6.2 | 18.4 |
| 2 | 27.0 | 3.7 | 94.4 | 1712 | 0.944 | <0.01 | 55.6 | 138.6 |
| 3 | 27.0 | 37.0 | 89.8 | 90 | — | — | 15.8 | 30.8 |
| 4 | 27.0 | 22.2 | 88.6 | 132 | — | — | 77.5 | 154.0 |
| 5 | 27.0 | 9.3 | 90.3 | 378 | 0.950 | 0.007 | 78.7 | 167.9 |
| 6 | 27.0 | 7.4 | 91.7 | 561 | 0.930 | 2.42 | 34.4 | 76.0 |
| 7 | 27.0 | 7.4 | 90.5 | 485 | 0.919 | 43.7 | 18.6 | 37.7 |
| 8 | 27.0 | 10.2 | 89.4 | 314 | 0.892 | 950 | 7.9 | 15.9 |
| 9 | 27.0 | 74.1 | 87.3 | 35 | 0.947 | 0.004 | 66.4 | 174.7 |
| 10 | 27.0 | 83.3 | 77.0 | 15 | 0.916 | 11.9 | 24.5 | 63.8 |
| 11 | 27.0 | 9.3 | 90.6 | 395 | 0.948 | 0.004 | 69.5 | 152.1 |
| 12 | 27.0 | 7.4 | 91.6 | 558 | 0.897 | 640 | 8.6 | 17.7 |
| 13 | 27.0 | 6.5 | 89.5 | 496 | 0.945 | 0.004 | 66.6 | 154.6 |
| 14 | 27.0 | 9.3 | 69.5 | 93 | 0.948 | 0.003 | 94.9 | 205.0 |
| 15-C | 27.0 | 37.0 | 55.5 | 13 | — | 880 | 2.7 | 10.0 |
| 16-C | 27.0 | 37.0 | 35.6 | 6 | — | — | 1.8 | 7.5 |
| 17-C | 27.0 | 37.0 | 37.4 | 6 | — | 620 | 3.3 | 12.0 |
| 18-C | 27.0 | 37.0 | 94.6 | 179 | — | 1300 | 3.9 | 14.0 |
| 19-C | 27.0 | 37.0 | 94.8 | 186 | 0.925 | very high | 2.6 | 10.0 |

C = Comparative

What is claimed is:

1. A process for the solution polymerization of ethylene at a temperature of from 80° C. to 250° C. and a total pressure of less than 25 mega Pascals in the presence of a catalyst system comprising:
   (1) an unbridged catalyst compound defined by the formula:

$^I$CpMLX$_n$ wherein:
   $^I$Cp is a cyclic ligand which forms a delocalized pi-bond with M;
   M is a metal selected from the grout consisting of Ti, Hf and Zr;
   X is an activatable ligand;
   n is 2 when M is Hf and n is 1 or 2 when M is Ti or Zr;

8. The process of claim 1 wherein said ionic activator is a cation/anion complex which contains a carbonium, oxonium or sulfonium cation and wherein said anion is a bulky, labile anion which is not coordinated to said M or is only loosely coordinated to said M.

9. The process of claim 1 wherein said solution polymerization is a copolymerization of ethylene with at least one copolymerizable alpha olefin.

10. The process of claim 9 wherein said alpha olefin is selected from the group consisting of butene and octene.

11. The process of claim 1 when undertaken at a temperature of from 120° C. to 220° C.

12. The process of claim 1 wherein said unbridged catalyst compound is cyclopentadienyl(tri-iso-propylsiloxy) titanium dimethyl and said ionic activator is triphenylcarbenium tetrakis (pentafluorophenyl) borate.

* * * * *